US012649910B2

(12) United States Patent
Han et al.

(10) Patent No.: US 12,649,910 B2
(45) Date of Patent: Jun. 9, 2026

(54) CYCLODEXTRIN GLYCOSYLTRANSFERASE WITH ENHANCED SOLVENT TOLERANCE AND PREPARATION THEREOF

(71) Applicant: Jiangnan University, Wuxi (CN)

(72) Inventors: Ruizhi Han, Wuxi (CN); Ye Ni, Wuxi (CN); Yulin Jiang, Wuxi (CN); Zhaoyue Fan, Wuxi (CN)

(73) Assignee: Jiangnan University, Wuxi (CN)

( * ) Notice: Subject to any disclaimer, the term of this patent is extended or adjusted under 35 U.S.C. 154(b) by 338 days.

(21) Appl. No.: 18/422,227

(22) Filed: Jan. 25, 2024

(65) Prior Publication Data

US 2024/0200039 A1     Jun. 20, 2024

Related U.S. Application Data

(63) Continuation of application No. PCT/CN2023/102014, filed on Jun. 25, 2023.

(30) Foreign Application Priority Data

Sep. 1, 2022    (CN) .......................... 202211071304.8

(51) Int. Cl.
*C12N 9/10* (2006.01)
*C12N 15/70* (2006.01)
*C12P 17/06* (2006.01)

(52) U.S. Cl.
CPC ........... *C12N 9/1074* (2013.01); *C12N 15/70* (2013.01); *C12P 17/06* (2013.01); *C12Y 204/01019* (2013.01)

(58) Field of Classification Search
CPC .... C12N 9/1074; C12N 15/70; C12N 9/1048; C12P 17/06; C12P 19/18; C12P 19/60; C12Y 204/01019
See application file for complete search history.

(56) References Cited

FOREIGN PATENT DOCUMENTS

| CN | 103484439 A | 1/2014 |
| CN | 113817704 A | 12/2021 |
| CN | 116144622 A | 5/2023 |
| WO | 0202725 A1 | 1/2002 |

OTHER PUBLICATIONS

UniProt Accession No. O72766_PAEMA (2 pages, Jun. 2021) (Year: 2021).*
Han, Ruizhi et. al. "high production of genistein diglucoside derivative using cyclodextrin glycosyltransferase from Paenibacillus macerans" J. Ind Microbiol Biotechnol. 44, 1343 1354, Jun. 28, 2017.
Chai, Baocheng, et. a. "Engineering of the 182 site of cyclodextrin glucosyltransferase for glycosylated genistein synthesis " Chinese J of Biotechnology. 38(2) 749-759, Feb. 25, 2022.
Ronald M. A. Knegtel et. al. "Crystal structure of 2.3 A resolution and Revised nucleotide sequence of the thermostable cyclodextrin clycosyltransferase from thermoanaerobacterium thermosulfurigenes EM1" J. Mol. Biol. V256 No. 3 Mar. 1, 1996, p. 611-622.

* cited by examiner

*Primary Examiner* — David Steadman
*Assistant Examiner* — Joseph R Spangler
(74) *Attorney, Agent, or Firm* — IPro, PLLC

(57) ABSTRACT
The disclosure discloses a cyclodextrin glycosyltransferase with enhanced solvent tolerance and preparation thereof, belonging to the technical fields of enzyme engineering and genetic engineering. The disclosure constructs four cyclodextrin glycosyltransferase mutants with enhanced organic solvent tolerance. Among them, the mutant with the optimal tolerance to DMSO and methanol is G539I/R146F/D147N, which is 1.6 times and 1.7 times higher than that of WT, respectively; the mutant with the optimal tolerance to ethanol is R146F, which is 1.4 times higher than that of WT; the mutant with the optimal tolerance to acetone is G539I/R146F, which is 1.5 times higher than that of WT. The disclosure helps to expand the application of glycosyltransferases in organic reaction systems, improves the enzymatic efficiency of CGTase on natural hydrophobic substrates, and has great application prospects.

4 Claims, 1 Drawing Sheet

Specification includes a Sequence Listing.

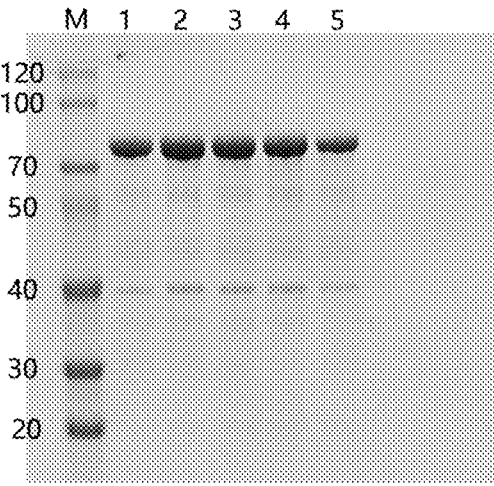

CYCLODEXTRIN GLYCOSYLTRANSFERASE WITH ENHANCED SOLVENT TOLERANCE AND PREPARATION THEREOF

REFERENCE TO SEQUENCE LISTING

The instant application contains a Sequence Listing in XML format as a file named "YGHY-2023-42-SEQ.xml", created on Jan. 15, 2024, of 35,743 bytes in size, and which is hereby incorporated by reference in its entirety.

TECHNICAL FIELD

The disclosure relates to a cyclodextrin glycosyltransferase with enhanced solvent tolerance and preparation thereof, belonging to the technical fields of enzyme engineering and genetic engineering.

BACKGROUND

Cyclodextrin glycosyltransferase (CGTase, EC 2.4.1.19) belonging to the α-amylase family has great commercial value due to its diverse transglycosylation activity (cyclization, disproportionation, coupling activity). Currently, this enzyme is mainly used for producing cyclodextrins in industry. In addition, this enzyme also has partial hydrolysis activity and plays an important role in short chain glycosylation reaction process. In recent years, good progress has been made in enhancing the properties of natural substrates (such as solubility, stability, etc.) by utilizing their transglycosylation activity, such as L-ascorbic acid, rutin, genistein, etc. Most glycosylation products maintain the excellent properties and value of the substance itself, thus they have good applications in various fields such as food and chemical engineering.

At present, the molecular modification of cyclodextrin glycosyltransferase mainly focuses on the properties such as catalytic activity, thermal stability, and specificity and has made good progress. However, for enzymatic reactions, their catalytic efficiency is not only related to the enzyme itself, but also to the environment of the enzyme. In industrial production, the use of organic solvents is extremely important, and the biological conversion of many hydrophobic substrates relies on the organic solvents.

Similar to most enzymes, the enzyme activity and enzyme stability of natural cyclodextrin glycosyltransferase in organic solvent environments are greatly affected. Therefore, in order to overcome this bottleneck, it is of great significance to enhance the organic solvent tolerance and enzyme activity of cyclodextrin glycosyltransferase through molecular modification strategies.

SUMMARY

The purpose of the disclosure is to provide a cyclodextrin glycosyltransferase mutant with enhanced solvent tolerance, which is beneficial to expand the glycosylation application of cyclodextrin glycosyltransferase to natural hydrophobic substrates.

The mutant is obtained by mutating the amino acids at positions 146, 147, and 539 of the cyclodextrin glycosyltransferase with an amino acid sequence as shown in SEQ ID NO. 1.

In one embodiment of the disclosure, the cyclodextrin glycosyltransferase is derived from *Paenibacillus macerans*.

In one embodiment of the disclosure, the nucleotide sequence of the cyclodextrin glycosyltransferase is shown in SEQ ID NO. 2.

In one embodiment of the disclosure, the mutant is obtained by mutating arginine at position 146 of the cyclodextrin glycosyltransferase with an amino acid sequence as shown in SEQ ID NO. 1 to phenylalanine, named R146F, with an amino acid sequence as shown in SEQ ID NO. 3 and a nucleotide sequence as shown in SEQ ID NO. 4.

In one embodiment of the disclosure, the mutant is obtained by mutating glycine at position 539 of the cyclodextrin glycosyltransferase with an amino acid sequence as shown in SEQ ID NO. 1 to isoleucine, named G539I, with an amino acid sequence as shown in SEQ ID NO. 5 and a nucleotide sequence as shown in SEQ ID NO. 6.

In one embodiment of the disclosure, the mutant is obtained by mutating glycine at position 539 of the cyclodextrin glycosyltransferase with an amino acid sequence as shown in SEQ ID NO. 1 to isoleucine and arginine at position 146 to phenylalanine, named G539I/R146F, with an amino acid sequence as shown in SEQ ID NO. 7 and a nucleotide sequence as shown in SEQ ID NO. 8.

In one embodiment of the disclosure, the mutant is obtained by mutating glycine at position 539 of the cyclodextrin glycosyltransferase with an amino acid sequence as shown in SEQ ID NO. 1 to isoleucine, arginine at position 146 to phenylalanine, and aspartate at position 147 to asparagine; named G539I/R146F/D147N, with an amino acid sequence shown in SEQ ID NO. 9 and a nucleotide sequence as shown in SEQ ID NO. 10.

The disclosure further provides a gene encoding the above mutant.

The disclosure further provides a recombinant vector carrying the above gene.

In one embodiment of the disclosure, the vector is a pET series vector, a pUT series vector, or a pBAD series vector.

The disclosure further provides a recombinant cell expressing the above mutant, or carrying the above gene, or carrying the above recombinant vector.

In one embodiment of the disclosure, the recombinant cell uses fungi or bacteria as a host cell.

In one embodiment of the disclosure, the host cell is either *Escherichia coli* or *Bacillus subtilis*.

The disclosure further provides a method for preparing the cyclodextrin glycosyltransferase mutant, including the following specific steps:

(1) Firstly, primers for site-specific mutation are designed. A plasmid containing the cyclodextrin glycosyltransferase gene is used as a template for full plasmid PCR. After digesting the template, a recombinant plasmid carrying the mutation gene is obtained and transferred to the host bacterium. After resistance screening with kanamycin, the strain is selected for cultivation and sent for sequencing.

(2) The correctly sequenced strains are cultured, incubated at 37° C. for 12 h, and transferred to a TB culture medium at an inoculum size of 1%. The cultivation is carried out at 37° C. until the OD grows to about 0.8, and then the induced expression is carried out at 16° C. for 18 h.

(3) After the cultivation is completed, the collected fermentation broth is centrifuged to collect the bacterial cells, subjected to ultrasonic crushing, and centrifuged again. The collected supernatant is a crude enzyme solution of the mutant.

In one embodiment of the disclosure, the recombinant plasmid uses pET-28a (+) as an expression vector.

In one embodiment of the disclosure, the host bacterium is *E. Coli* BL21 (DE3).

In one embodiment of the disclosure, the organic solvent includes dimethyl sulfoxide (DMSO), ethanol, methanol, and acetone.

The disclosure further provides a method for enhancing the tolerance of the cyclodextrin glycosyltransferase to organic solvents. The method includes mutating glycine at position 539 of the cyclodextrin glycosyltransferase with an amino acid sequence as shown in SEQ ID NO. 1 to isoleucine;

or mutating glycine at position 539 of the cyclodextrin glycosyltransferase with an amino acid sequence as shown in SEQ ID NO. 1 to isoleucine and arginine at position 146 to phenylalanine;

or mutating glycine at position 539 of the cyclodextrin glycosyltransferase with an amino acid sequence as shown in SEQ ID NO. 1 to isoleucine, arginine at position 146 to phenylalanine and aspartate at position 147 to asparagine.

In one embodiment of the disclosure, the organic solvent includes one or more of dimethyl sulfoxide (DMSO), ethanol, methanol, and acetone.

The disclosure further provides a method for producing long-chain glycosylated genistein, where the method includes adding the cyclodextrin glycosyltransferase mutant to a reaction system containing soluble starch and genistein for reaction to obtain a reaction solution and separating the reaction solution to obtain the long-chain glycosylated genistein.

The disclosure further provides the glycosylation application of the above mutant, the above gene, the above recombinant vector, or the above recombinant cell in natural hydrophobic substrates, or the glycosylation application in some organic solvent reaction systems.

Beneficial Effects (1) The disclosure constructs four cyclodextrin glycosyl-transferase mutants with enhanced organic solvent tolerance, R146F, G539I, G539I/R146F, and G539I/R146F/D147N, whose original activity directly measured in a system without organic solvents remains at 90% to 120% of WT activity.

(2) In the determination of tolerance to dimethyl sulfoxide, the residual activity of WT remains at 21.3% after incubation in a 25% DMSO system for 1 h. The tolerance of the mutants R146F, G539I, G539I/R146F, and G539I/R146F/D147N is enhanced, and the mutant with the optimal tolerance to DMSO is G539I/R146F/D147N, which is 1.6 times higher than that of WT.

(3) In the determination of ethanol tolerance, the residual activity of WT incubated in 12% ethanol for 1 h is 17.9%. Under the same determination conditions for the four cyclodextrin glycosyltransferase mutants, it is found that the mutant with the optimal tolerance to methanol is R146F, which is 1.4 times higher than that of WT.

(4) In the determination of methanol tolerance, the residual activity of WT incubated in 12% methanol for 1 h is 27.4%. Under the same determination conditions for the four cyclodextrin glycosyltransferase mutants, it is found that the mutant with the optimal tolerance to methanol is G539I/R146F/D147N, which is 1.7 times higher than that of WT.

(5) In the determination of tolerance to acetone, the residual activity of WT incubated in 15% acetone for 1 h is 22.3%. Under the same determination conditions for the four cyclodextrin glycosyltransferase mutants, it is found that the mutant with the optimal tolerance to acetone is G539I/R146F, which is 1.5 times higher than that of WT.

(6) The disclosure has obtained two cyclodextrin glyco-syltransferase mutants with enhanced organic solvent tolerance, enhancing the glycosylation efficiency of hydrophobic substrates, helping to expand the industrial application range of CGTase, and having great application prospects.

BRIEF DESCRIPTION OF FIGURES

FIG. 1 is a protein gel map of wild-type and mutant pure enzymes; in the FIGURE, M: Marker; 1: R146F; 2: G539I; 3: G539I/R146F; 4: G539I/R146F/D147N; and 5: Wild-type (WT).

DETAILED DESCRIPTION

The specific examples of the disclosure are only used for further explanation and cannot be used as limiting content or scope of the disclosure.

The primer sequences involved in the following examples are shown in Table 1.

TABLE 1

| Primers | |
| --- | --- |
| Name | Primer sequence (5'→3') |
| R146F | F: TCTCCGGCAGATTTTGACAATCCG (SEQ ID NO. 11) |
| | R: CGGATTGTCAAAATCTGCCGGAGA (SEQ ID NO. 12) |
| G539I | F: ACCGCGGTCACCATTAGTGGTATT (SEQ ID NO. 13) |
| | R: AATACCACTAATGGTGACCGCGGT (SEQ ID NO. 14) |
| G539I/R146F | F1: TCTCCGGCAGATTTTGACAATCCG (SEQ ID NO. 15) |
| | R1: CGGATTGTCAAAATCTGCCGGAGA (SEQ ID NO. 16) |
| | F2: ACCGCGGTCACCATTAGTGGTATT (SEQ ID NO. 17) |
| | R2: AATACCACTAATGGTGACCGCGGT (SEQ ID NO. 18) |
| G539I/R146F/D147N | F1: TCTCCGGCAGATTTTAATAATCCG (SEQ ID NO. 19) |
| | R1: CGGATTATTAAAATCTGCCGGAGA (SEQ ID NO. 20) |
| | F2: ACCGCGGTCACCATTAGTGGTATT (SEQ ID NO. 21) |
| | R2: AATACCACTAATGGTGACCGCGGT (SEQ ID NO. 22) |

The Culture Media Involved in the Following Examples are as Follows:

LB liquid culture medium: yeast powder 5.0 g·L$^{-1}$, tryptone 10.0 g·L$^{-1}$, and NaCl 10.0 g·L$^{-1}$.

LB solid culture medium: 2% agar is added to the LB liquid culture medium.

TB liquid culture medium: yeast powder 24.0 g·L$^{-1}$, tryptone 12.0 g·L$^{-1}$, KH$_2$PO$_3$ 2.3 g·L$^{-1}$, K$_2$HPO$_3$ 16.4 g·L$^{-1}$, and glycerol 5 g·L$^{-1}$.

The Detection Methods Involved in the Following Examples are as Follows:

Activity Detection of Cyclodextrin Glycosyltransferase:

Cyclization activity measurement with methyl orange method: 50 μL of the cyclodextrin glycosyltransferase is taken for diluting to be an enzyme solution with an appropriate concentration. 200 μL of maltodextrin (the solution with a concentration of 10 g·L$^{-1}$ is prepared with 50 mM phosphate buffer (pH 6.0) in advance) is added. The reaction is carried out in a shaker at 40° C. for 10 min by water bath. 250 μL of hydrochloric acid (1.0 M) is immediately added to terminate the reaction. 150 μL of the methyl orange (the solution with a concentration of 0.5 mM is prepared with 50 mM phosphate buffer) is added and allowed to stand at room temperature (20° C.) for 20 min. The absorbance is measured at 505 nm. The group without enzyme solution is used as the blank control.

Definition of enzyme activity: The amount of enzyme required for generating 1 μmol α-cyclodextrin per min is defined as one enzyme activity unit.

The construction method of the T599D/N600D/Y601H mutant pure enzyme involved in the following examples is recorded in the Chinese invention patent application file with a publication number of CN113817704A.

Example 1: Preparation and Expression of Cyclodextrin Glycosyltransferase Mutant 1. Site-Specific Mutation (1) Construction of pET28a (+)-cgt The Specific Steps are as Follows:

Glycerol bacteria *E. Coli* BL21 (DE3)/pET-20b (+)-cgt preserved in laboratory was taken. The strain *E. Coli* BL21 (DE3)/pET-20b (+)-cgt was prepared by enzyme digestion of pET-20b (+) with a cyclodextrin glycosyltransferase cgt with a nucleotide sequence as shown in SEQ ID NO. 2 and ligation so as to obtain a recombinant plasmid. The recombinant plasmid was imported into *E. coli* BL21 (DE3) to prepare sufficient bacteria. The specific construction process can be seen in the reference: Han, R., Ge, B., Jiang, M. et al. High production of genistein diglucoside derivative using cyclodextrin glycosyltransferase from *Paenibacillus macerans*. J Ind Microbiol Biotechnol 44, 1343-1354 (2017).

*E. Coli* BL21 (DE3)/pET-20b (+)-cgt was subjected to streak for activation, and a single colony was picked and inoculated in a LB liquid culture medium containing ampicillin (100 mg/L). After 10 h of cultivation at 37° C., the plasmid pET-20b (+)-cgt was extracted using a reagent kit.

One step cloning and vector replacement: The primers were designed with primer sequences: F: CAGCAAATGGGTCGCGGATCCTCACCGGACACCTCAGTGGA (SEQ ID NO.23) and R: GTGGTGGTGGTGGTGCTCGAGATTTTGCCAATCCACCGTCA (SEQ ID NO.24). A large number of cloned target fragments were obtained using the plasmid pET-20b (+)-cgt as a template through PCR technology. After gel recovery, they were linked to the plasmid pET-28a (+) after double enzyme digestion (Bam HI and Xho I), and transferred to *E. coli*

BL21 for coating and cultivation. After the colony significantly grew, the colony was picked and transferred to the LB liquid culture medium for cultivation for 10 h. The plasmid was extracted and sent for sequencing, and the plasmid with correct sequencing was labeled as pET-28a (+)-cgt.

(2) Construction of Mutants

The amino acid sequence of the cyclodextrin glycosyltransferase in the disclosure is as shown in SEQ ID NO. 1 (the nucleotide sequence of the gene is as shown in SEQ ID NO. 2). Primers are designed based on the selected mutation sites. The extracted recombinant plasmid pET28a (+)-cgt is used as a template for full plasmid PCR. The primer sequences are as follows:

Primers used for mutant R146F:

Forward primer: 5'-TCTCCGGCAGAT-TTTGACAATCCG-3' (SEQ ID NO. 11), with the underline indicating the mutated base; and reverse primer: 5'-CGGATTGTCAAAATCTGCCG-GAGA-3' (SEQ ID NO. 12), with the underline indicating the mutated base.

Primers used for mutant G539I:

Forward primer: 5'-ACCGCGGTCACCATTAGTGGT-ATT-3' (SEQ ID NO. 13), with the underline indicating the mutated base; and reverse primer: 5'-AATAC-CACTAATGGTGACCGCGGT-3' (SEQ ID NO. 14), with the underline indicating the mutated base.

Primers used for mutant G539I/R146F:

Forward primer 1: 5'-TCTCCGGCAGAT-TTTGACAATCCG-3' (SEQ ID NO. 15), with the underline indicating the mutated base; and reverse primer 1: 5'-CGGATTGTCAAAATCTGCCG-GAGA-3' (SEQ ID NO. 16), with the underline indicating the mutated base.

Forward primer 2: 5'-ACCGCGGTCACCATTAGTGGT-ATT-3' (SEQ ID NO. 17), with the underline indicating the mutated base; and reverse primer 2: 5'-AATAC-CACTAATGGTGACCGCGGT-3' (SEQ ID NO. 18), with the underline indicating the mutated base.

Primers used for mutant G539I/R146F/D147N:

Forward primer 1: 5'-TCTCCGGCAGAT TTTAATAATCCG-3' (SEQ ID NO. 19), with the underline indicating the mutated base; and reverse primer 1: 5'-CGGATTATTAAAATCTGCCG-GAGA-3' (SEQ ID NO. 20), with the underline indicating the mutated base.

Forward primer 2: 5'-ACCGCGGTCACCATTAGTGGT-ATT-3' (SEQ ID NO. 21), with the underline indicating the mutated base; and reverse primer 2: 5'-AATAC-CACTAATGGTGACCGCGGT-3' (SEQ ID NO. 22), with the underline indicating the mutated base.

The PCR reaction systems were all: 5 μL of 5×Prime-STAR Buffer (Mg$^{2+}$ Plus), 4 μL of 2.5 mM dNTPs, 1 μL of 10 μM forward primer, 1 μL of 10 UM reverse primer, 1 μL of Template DNA, and 0.5 μL of 2.5 U/μL PrimeSTAR Taq HS. Double distilled water was added to replenish to 50 μL.

The amplification conditions of PCR products were as follows: Pre-denaturation was carried out at 98° C. for 5 min; at 98° C. for 10 s, at 50° C. for 15 s, and at 68° C. for 4 min, after 25 cycles, the temperature was kept at 68° C. for 10 min, and the products were finally stored at 16° C.

1% agarose gel electrophoresis was used to detect PCR products. After correct detection, digestive enzyme (Dpn I)

was added for digesting the template. The template was digested at 37° C. for 1 h. The products obtained by digestion were transferred into competent *E. coli* BL21, and cultured overnight in a LB solid culture medium containing 50 mg/L kanamycin. Positive clones were picked out and cultured in a LB liquid culture medium for 10 h. The plasmids were extracted and sent for sequencing. If the sequencing is correct, recombinant *E. coli* that can express mutants was obtained, that is, recombinant *E. coli* was prepared: *E. coli* BL21(DE3)/pET28a(+)-R146F, *E. coli* BL21(DE3)/pET28a(+)-G539I, *E. coli* BL21(DE3)/pET28a(+)-G539I/R146F, *E. coli* BL21(DE3)/pET28a(+)-G539I/R146F/D147N.

(3) Construction of Recombinant Bacteria Containing Wild-Type CGTase

The recombinant plasmid pET28a (+)-cgt was imported into *E. coli* BL21 (DE3) according to the above method, and *E. Coli* BL21 (DE3)/pET-28a (+)-cgt was obtained.

2. Expression of Mutants

Recombinant *E. coli* containing mutant genes and wild-type strain *E. Coli* BL21 (DE3)/pET-28a (+)-cgt obtained in step 1 were added to a LB liquid culture medium (containing kanamycin, 50 mg/L), and cultured at 37° C. for 10 h to prepare a seed solution.

The obtained seed solution was injected into the TB liquid culture medium (containing kanamycin, 50 mg/L) at an inoculum size of 1% (v/v), cultured in a shaker at 37° C. until the $OD_{600}$ reached 0.6-0.8, and induced expression with IPTG with a final concentration of 0.1 mM was carried out. After 18 h of fermentation cultivation at 16° C., a fermentation broth was obtained.

The prepared fermentation broth was centrifuged at 4° C. and 8000 r/min for 10 min for collecting bacterial cells. The supernatant was poured out. The remaining precipitate was resuspended with phosphate buffer (pH 6.0, 50 mM) for ultrasonic disruption at 300 W for 10 min. The disruption solution was centrifuged at 4° C. and 8000 r/min for 30 min to obtain the supernatant, which is the crude enzyme solution containing the mutant. The crude enzyme solution containing wild-type CGTase, the crude enzyme solution containing R146F, and the crude enzyme solution containing G539I, the crude enzyme solution containing G539I/R146F and the crude enzyme solution containing G539I/R146F/D147N were obtained.

Agarose gel electrophoresis was carried out on the crude enzyme solution of the mutant and the crude enzyme solution of the wild-type enzyme to verify the successful expression of the protein.

3. Purification of Mutants and Wild-Type Enzymes

The above crude enzyme solution was treated through membrane and Ni column affinity chromatography purification was carried out. First, the Ni column was equilibrated with buffer A (containing 20 mM sodium phosphate, 0.5 M sodium chloride, 20 mM imidazole, and pH 7.4). After equilibrium, the protein sample was loaded for multiple times to fully being adsorbed. Then, gradient elution was carried out successively with imidazole solutions of different concentrations (20-500 mM) and eluents were collected. After completion, 10% protein gel was prepared to detect the target protein, and imidazole solutions containing the target protein were merged, and concentration and replacement were carried out with an ultrafiltration tube and phosphate buffer with pH 6.0. Finally, the obtained protein sample was divided, frozen with liquid nitrogen, and stored at −80° C. for later use.

Pure enzyme solutions containing wild-type CGTase, R146F, G539I, G539I/R146F, and G539I/R146F/D147N were prepared, respectively.

Agarose gel electrophoresis was carried out on the above mutant and wild-type enzyme solutions respectively. The results are shown in FIG. 1. There are corresponding bands at 74 kDa (the third band of Marker is 70 kDa).

Example 2: Organic Solvent Tolerance Detection of Cyclodextrin Glycosyltransferase In the embodiment of the disclosure, the organic solvent tolerance of cyclodextrin glycosyltransferase was analyzed by measuring its residual enzyme activity after incubation in different concentrations of organic solvents for a certain period of time.

Calculation of residual activity = enzyme activity after incubation (enzyme activity measured in organic solvent systems with different concentrations)/enzyme activity without incubation (enzyme activity measured in *PBS* systems).

The Specific Steps are as Follows:

1. Detection of Organic Solvent Dimethyl Sulfoxide (DMSO) Tolerance of Cyclodextrin Glycosyltransferase The dimethyl sulfoxide with the concentrations of 0% and 25% (v/v) was selected, respectively. The incubation time was controlled at 1 h, and the activity of the obtained pure enzyme was measured using the methyl orange method (which was appropriately improved for easy detection).

The specific methods are as follows:

(1) The pure enzyme solution prepared in Example 1 and the T599D/N600D/Y601H mutant pure enzyme solution were diluted to an enzyme activity of 0.01-0.02 mg/ml, then 100 μL of each of the two pure enzyme solutions was taken and added to a 100 μL of phosphate buffer containing DMSO (50 mM, pH 6.0). The initial volume fractions of DMSO in the phosphate buffer containing DMSO are 0% and 50%, respectively.

(2) Preparation of maltodextrin solution: 50 mM phosphate buffer (pH 6.0) was used to prepare a maltodextrin solution with a concentration of 40 g·L$^{-1}$ from maltodextrin.

Preparation of methyl orange solution: A methyl orange solution with a concentration of 0.5 mM was prepared with methyl orange using 50 mM phosphate buffer.

(3) After incubating the system obtained in step (1) at 4° C. for 1 h, 50 μL of the maltodextrin solution prepared in step (2) was added. After reacting at 40° C. for 10 min, 250 μL of hydrochloric acid (1.0 M) was immediately added to terminate the reaction. Then, 150 μL of the methyl orange solution prepared in step (2) was added and allowed to stand at room temperature for 20 min. The absorbance was measured at 505 nm.

The enzyme activity measured in the 0% (v/v) DMSO group was used as the original activity. The residual activity and relative activity of wild-type WT and mutants measured after incubation in 25% (v/v) DMSO are listed in Table 2.

TABLE 2

| | Relative activity (%) | Residual activity (%) |
|---|---|---|
| | Comparison of residual activity and relative activity between wild-type WT and mutants | |
| Sample | 0% DMSO | 25% DMSO |
| WT | 100 | 21.3 ± 4.7 |
| R146F | 91.1 ± 5.5 | 28.1 ± 3.2 |
| G539I | 85.5 ± 3.2 | 27.4 ± 2.5 |
| G539I/R146F | 93.1 ± 1.2 | 31.8 ± 2.3 |
| G539I/R146F/D147N | 120.2 ± 2.3 | 35.1 ± 3.7 |
| T599D/N600D/Y601H | 75.4 ± 4.3 | 33.7 ± 2.9 |

From Table 2, it can be seen that after incubation at 4° C. for 1 h in a 25% DMSO system, the residual activity of WT is 21.3%. Compared to WT, the DMSO tolerance of the four mutants is improved to some extent. The tolerance of single mutants R146F and G539I is 6%-7% higher than that of WT after incubating in 25% DMSO for 1 h. The tolerance of the combined double mutant G539I/R146F is improved, which is 10.5% higher than that of WT. The tolerance of the optimal triple mutant G539I/R146F/D147N is 13.8% higher than that of WT under the same incubation conditions, which is 1.6 times higher than that of WT. The mutant T599D/N600D/Y601H also has good tolerance in a 25% DMSO system, and the effect of this triple mutant is similar to the optimal triple mutant G539I/R146F/D147N.

In addition, except for the mutant G539I, the relative activity of the other three mutants is not significantly affected compared to WT. However, as for the mutant T599D/N600D/Y601H, although the DMSO resistance of the mutant is also significantly enhanced, the original activity of the mutant significantly decreases. The activity of the triple mutant G539I/R146F/D147N is 20% higher than that of WT. Therefore, the triple mutant G539I/R146F/D147N may have more advantages in practical applications.

2. Detection of Organic Solvent Ethanol Tolerance of Cyclodextrin Glycosyltransferase The ethanol with the concentrations of 0% and 12% (v/v) was selected, respectively. The incubation time was controlled at 1 h, and the activity of the obtained pure enzyme was measured using the methyl orange method (which was appropriately improved for easy detection).

The specific methods are as follows:

(1) The pure enzyme solution prepared in Example 1 and the T599D/N600D/Y601H mutant pure enzyme solution were diluted to an enzyme activity of 0.01-0.02 mg/mL, then 100 μL of each of the two pure enzyme solutions was taken and added to a 100 μL of phosphate buffer containing ethanol (50 mM, pH 6.0). The volume fractions of ethanol in the phosphate buffer containing ethanol are 0% and 24%, respectively.

(2) Preparation of maltodextrin solution: 50 mM phosphate buffer (pH 6.0) was used to prepare a maltodextrin solution with a concentration of 40 g·L⁻¹ from maltodextrin.

Preparation of methyl orange solution: A methyl orange solution with a concentration of 0.5 mM was prepared with methyl orange using 50 mM phosphate buffer.

(3) After incubating the system obtained in step (1) at 4° C. for 1 h, 50 μL of the maltodextrin solution prepared in step (2) was added. After reacting at 40° C. for 10 min, 250 μL of hydrochloric acid (1.0 M) was immediately added to terminate the reaction. Then, 150 μL of the methyl orange solution prepared in step (2) was added and allowed to stand at room temperature for 20 min. The absorbance was measured at 505 nm.

The enzyme activity measured in the 0% (v/v) ethanol group was used as the original activity. The residual activity and relative activity of wild-type WT and mutants measured after incubation in 12% (v/v) ethanol are listed in Table 3.

TABLE 3

| | Relative activity (%) | Residual activity (%) |
|---|---|---|
| | Comparison of residual activity and relative activity between wild-type WT and mutants | |
| Sample | 0% ethanol | 12% ethanol |
| WT | 100 | 17.9 ± 4.5 |
| R146F | 98.5 ± 2.7 | 25.3 ± 4.0 |
| G539I | 87.5 ± 4.1 | 23.8 ± 2.2 |
| G539I/R146F | 90.7 ± 3.2 | 22.8 ± 3.4 |
| G539I/R146F/D147N | 115.2 ± 4.5 | 20.7 ± 2.7 |
| T599D/N600D/Y601H | 72.2 ± 3.6 | 21.9 ± 3.0 |

From Table 3, it can be seen that after incubation at 4° C. for 1 h in a 12% ethanol system, the residual activity of WT is 17.9%. Compared to WT, the ethanol tolerance of the two single mutants is significantly improved. The tolerance of the optimal single mutant R146F is 7.4% higher than that of WT, which is 1.4 times higher than that of WT, the ethanol tolerance of the single mutant G539I is 5.9% higher than that of WT. However, the tolerance of the two combined mutants in ethanol is not significantly improved compared to WT. The tolerance of the mutant T599D/N600D/Y601H in 12% ethanol is similar to that of the two combined mutants mentioned above, and the effect is not significant. This may also be related to a significant decrease in the original activity of the mutant. In addition, compared to the data of DMSO, it is found that the enzyme has poor tolerance to ethanol.

In addition, in terms of enzyme activity, the relative activity of the four mutants in the disclosure does not significantly decrease compared to WT, and the relative activity remains between 87% and 115%. The activity of the triple mutant G539I/R146F/D147N is improved compared to WT.

3. Detection of Organic Solvent Methanol Tolerance of Cyclodextrin Glycosyltransferase The methanol with the concentrations of 0% and 12% (v/v) was selected, respectively. The incubation time was controlled at 1 h, and the activity of the obtained pure enzyme was measured using the methyl orange method (which was appropriately improved for easy detection).

The specific methods are as follows:

(1) The pure enzyme solution prepared in Example 1 and the T599D/N600D/Y601H mutant pure enzyme solution were diluted to an enzyme activity of 0.01-0.02 mg/mL, then 100 μL of each of the two pure enzyme solutions was taken and added to a 100 μL of phosphate buffer containing methanol (50 mM, pH 6.0). The volume fractions of methanol in the phosphate buffer containing methanol are 0% and 24%, respectively.

(2) Preparation of maltodextrin solution: 50 mM phosphate buffer (pH 6.0) was used to prepare a maltodextrin solution with a concentration of 40 g·L⁻¹ from maltodextrin.

Preparation of methyl orange solution: A methyl orange solution with a concentration of 0.5 mM was prepared with methyl orange using 50 mM phosphate buffer.

(3) After incubating the system obtained in step (1) at 4° C. for 1 h, 50 μL of the maltodextrin solution prepared in step (2) was added. After reacting at 40° C. for 10 min, 250 μL of hydrochloric acid (1.0 M) was immediately added to terminate the reaction. Then, 150 μL of the methyl orange solution prepared in step (2) was added and allowed to stand at room temperature for 20 min. The absorbance was measured at 505 nm.

The enzyme activity measured in the 0% (v/v) methanol group was used as the original activity. The residual activity and relative activity of wild-type WT and mutants measured after incubation in 12% (v/v) methanol are listed in Table 4.

TABLE 4

Comparison of residual activity and relative activity between wild-type WT and mutants

| Sample | Relative activity (%) 0% methanol | Residual activity (%) 12% methanol |
|---|---|---|
| WT | 100 | 27.4 ± 2.3 |
| R146F | 89.2 ± 3.4 | 40.1 ± 2.7 |
| G539I | 90.6 ± 4.6 | 23.4 ± 3.0 |
| G539I/R146F | 94.8 ± 3.2 | 38.7 ± 3.6 |
| G539I/R146F/D147N | 113.2 ± 2.3 | 46.3 ± 4.5 |
| T599D/N600D/Y601H | 69.5 ± 3.9 | 34.3 ± 2.7 |

From Table 4, it can be seen that after incubation at 4° C. for 1 h in a 12% methanol system, the residual activity of WT is 27.4%. Compared to WT, the methanol tolerance of the single mutant R146F, the double mutant G539I/R146F, and the triple mutant G539I/R146F/D147N is significantly improved. The triple mutant has an optimal effect, which is nearly 1.7 times and 18.9% higher than that of WT, followed by the single mutant R146F and the double mutant G539I/R146F, which is 12.7% and 11.3% higher than that of WT, respectively. However, the tolerance of the single mutant G539I to methanol is not as good as WT. In addition, compared to the tolerance data of the single mutant R146F and the double mutant G539I/R146F, after adding G539I, the tolerance to methanol decreases. Therefore, the mutant R146F plays an important role in methanol tolerance detection. As for the mutant T599D/N600D/Y601H, its tolerance in 12% methanol is 6.9% higher than that of WT, but its effect is far less significant than the optimal triple mutant G539I/R146F/D147N.

In terms of enzyme activity, the relative activity of the four mutants does not significantly decrease compared to WT, and remains at 89-113%. The activity of the triple mutant G539I/R146F/D147N is improved compared to WT.

4. Detection of Organic Solvent Acetone Tolerance of Cyclodextrin Glycosyltransferase The acetone with the concentrations of 0% and 15% (v/v) was selected, respectively. The incubation time was controlled at 1 h, and the activity of the obtained pure enzyme was measured using the methyl orange method (which was appropriately improved for easy detection).

The specific methods are as follows:

(1) The pure enzyme solution prepared in Example 1 and the T599D/N600D/Y601H mutant pure enzyme solution were diluted to an enzyme activity of 0.01-0.02 mg/mL, then 100 μL of each of the two pure enzyme solutions was taken and added to a 100 μL of phosphate buffer containing acetone (50 mM, pH 6.0). The volume fractions of acetone in the phosphate buffer containing acetone are 0% and 30%, respectively.

(2) Preparation of maltodextrin solution: 50 mM phosphate buffer (pH 6.0) was used to prepare a maltodextrin solution with a concentration of 40 g·L⁻¹ from maltodextrin.

Preparation of methyl orange solution: A methyl orange solution with a concentration of 0.5 mM was prepared with methyl orange using 50 mM phosphate buffer.

(3) After incubating the system obtained in step (1) at 4° C. for 1 h, 50 μL of the maltodextrin solution prepared in step (2) was added. After reacting at 40° C. for 10 min, 250 μL of hydrochloric acid (1.0 M) was immediately added to terminate the reaction. Then, 150 UL of the methyl orange solution prepared in step (2) was added and allowed to stand at room temperature for 20 min. The absorbance was measured at 505 nm.

The enzyme activity measured in the 0% (v/v) acetone group was used as the original activity. The residual activity and relative activity of wild-type WT and mutants measured after incubation in 15% (v/v) acetone are listed in Table 5.

TABLE 5

Comparison of residual activity and relative activity between wild-type WT and mutants

| Sample | Relative activity (%) 0% acetone | Residual activity (%) 15% acetone |
|---|---|---|
| WT | 100 | 22.3 ± 3.2 |
| R146F | 92.8 ± 2.4 | 30.7 ± 3.8 |
| G539I | 87.2 ± 4.9 | 26.4 ± 2.5 |
| G539I/R146F | 97.1 ± 3.7 | 34.3 ± 3.2 |
| G539I/R146F/D147N | 117.2 ± 4.4 | 29.4 ± 4.6 |
| T599D/N600D/Y601H | 76.4 ± 3.4 | 26.6 ± 5.3 |

From Table 5, it can be seen that after incubation at 4° C. for 1 h in a 15% acetone system, the residual activity of WT is 22.3%. Compared to WT, the acetone tolerance of all four mutants is improved, and the tolerance of the optimal double mutant G539I/R146F is 12% higher than that of WT, which is 1.5 times higher than that of WT. In addition, the acetone tolerance of the single mutant R146F is similar to that of the triple mutant G539I/R146F/D147N, is 7%-8.4% higher than that of WT, while the acetone tolerance of the single mutant G539I and T599D/N600D/Y601H is not significantly improved compared to WT, only improved by about 4%.

In terms of enzyme activity which is consistent with previous results, the relative activity of the four mutants does not significantly decrease compared to WT, and remains at 87-117%. The activity of the triple mutant G539I/R146F/D147N is improved compared to WT.

Example 3: Glycosylation Application of Genistein

Taking genistein as an example, the mutant R146F, G539I, G539I/R146F, G539I/R146F/D147N pure enzyme solutions and the wild-type WT pure enzyme solution prepared in Example 1, and the mutant T599D/N600D/Y601H pure enzyme solution were diluted appropriately. Soluble starch was used as a glycosyl group donor and genistein was used as a glycosyl group acceptor for glycosylation reactions, respectively.

The specific steps are as follows:

(1) A soluble starch solution with a concentration of 40 g/L was prepared using a phosphate buffer (pH 6.0, 50 mM).

(2) The genistein was dissolved in a DMSO solution to obtain a genistein solution with a concentration of 7.5 g/L.

(3) Mixing was carried out according to the ratio of soluble starch solution:genistein solution:pure enzyme solution (v:v:v)=6:2:2 (with enzyme addition controlled at 0.15-0.2 U/mL), and reaction was carried out in a shaker at 40° C. for 16-18 h before heating to terminate the reaction.

After centrifugation and membrane treatment, the samples were analyzed by high performance liquid chromatography (HPLC), and the specific results are shown in Table 6.

TABLE 6

Comparison of glycosylation efficiency of genistein between wild-type WT and various mutants

| Sample | Conversion rate (%) |
| --- | --- |
| WT | 45 |
| R146F | 57 |
| G539I | 54 |
| G539I/R146F | 58 |
| G539I/R146F/D147N | 61 |
| T599D/N600D/Y601H | 46 |

From the above table, it can be seen that the four mutants in the disclosure have a certain improvement in the glycosylation efficiency of genistein compared to WT. The conversion rate of the optimal one triple mutant G539I/R146F/D147N is 16% higher than that of WT. The conversion rates of the remaining single mutant R146F, G539I, and double mutant G539I/R146F are 12%, 9%, and 13% higher than that of WT, respectively. Although the tolerance of the mutant T599D/N600D/Y601H in DMSO is significantly improved, it may be due to a significant decrease in enzyme activity, the performance in conversion rate is not significant, similar to WT, and there is no significant improvement.

Although the disclosure has been disclosed in preferred examples, it is not intended to limit the disclosure. Those skilled in the art can make various changes and modifications within the spirit and scope of the disclosure. Therefore, the scope of protection of the disclosure should be based on the scope defined in the claims.

What is claimed is:

1. A cyclodextrin glycosyltransferase mutant, wherein the mutant comprises the amino acid sequence of SEQ ID NO: 5, 7 or 9.

2. A recombinant cell comprising the cyclodextrin glycosyltransferase mutant according to claim 1.

3. The recombinant cell according to claim 2, wherein the recombinant cell is a fungal or bacterial host cell.

4. A method for producing long-chain glycosylated genistein, wherein the method comprises combining the cyclodextrin glycosyltransferase mutant according to claim 1 with soluble starch and genistein to thereby produce long-chain glycosylated genistein.

* * * * *

SEQUENCE LISTING

```
Sequence total quantity: 24
SEQ ID NO: 1            moltype = AA   length = 687
FEATURE                 Location/Qualifiers
source                  1..687
                        mol_type = protein
                        organism = synthetic construct
SEQUENCE: 1
SPDTSVDNKV NFSTDVIYQI VTDRFADGDR TNNPAGDAFS GDRSNLKLYF GGDWQGIIDK  60
INDGYLTGMG VTALWISQPV ENITSVIKYS GVNNTSYHGY WARDFKQTND AFGDFADFQN  120
LIDTAHAHNI KVVIDFAPNH TSPADRDNPG FAENGALYDN GSLLGAYSND TAGLFHHNGG  180
TDFSTIEDGI YKNLYDLADI NHNNNAMDAY FKSAIDLWLG MGVDGIRFDA VKHMPFGWQK  240
SFVSSIYGGD HPVFTFGEWY LGADQTDGDN IKFANESGMN LLDFEYAQEV REVFRDKTET  300
MKDLYEVLAS TESQYDYINN MVTFIDNHDM DRFQVAGSGT RATEQALALT LTSRGVPAIY  360
YGTEQYMTGD GDPNNRAMMT SFNTGTTAYK VIQALAPLRK SNPAIAYGTT TERWVNNDVL  420
IIERKFGSSA ALVAINRNSS AAYPISGLLS SLPAGTYSDV LNGLLNGNSI TVGSGGAVTN  480
FTLAAGGTAV WQYTAPETSP AIGNVGPTMG QPGNIVTIDG RGFGGTAGTV YFGTTAVTGS  540
GIVSWEDTQI KAVIPKVAAG KTGVSVKTSS GTASNTFKSF NVLTGDQVTV RFLVNQANTN  600
YGTNVYLVGN AAELGSWDPN KAIGPMYNQV IAKYPSWYYD VSVPAGTKLD FKFIKKGGGT  660
VTWEGGGNHT YTTPASGVGT VTVDWQN                                     687

SEQ ID NO: 2            moltype = DNA   length = 2061
FEATURE                 Location/Qualifiers
source                  1..2061
                        mol_type = other DNA
                        organism = synthetic construct
SEQUENCE: 2
tcaccggaca cctcagtgga caataaagtt aacttcagca ccgatgttat ctaccagatc  60
gtcacggacc gttttgcgga tggtgaccgc accaacaatc cggcaggcga tgctttcagc  120
ggtgaccgtt ctaatctgaa actgtatttt ggcggtgatt ggcagggcat tatcgataaa  180
attaacgacg gttacctgac cggcatgggt gtgacggcgc tgtggatcag ccaaccggtg  240
gaaaacatca cctcagttat caaatactcg ggcgtcaaca atacgtctta tcatggttac  300
tgggcccgtg attttaaaca gaccaacgac gcgtttggcg atttcgccga ctttcaaaat  360
ctgattgata ccgcacatgc tcacaacatt aaagtggtta tcgatttcgc cccgaaccac  420
acctctccgg cagatcgcga caatccgggc tttgcagaaa atggtgctct gtatgataac  480
ggctcactgc tgggtgcata ctcgaatgac accgctggcc tgttccatca caacggcggt  540
acggatttta gtaccattga agacggtatc tataaaaatc tgtacgatct ggctgacatc  600
aaccataaca ataacgcgat ggatgcctat ttcaaatcag caattgacct gtggctgggc  660
atgggtgttg atggcatccg ctttgacgcg gtcaaacaca tgccgttcgg ttggcagaaa  720
tcgtttgtga gcagcattta tggcggtgat caccggttca ttacccttcgg cgaatggtat  780
ctgggtgctg atcagacgga tggcgacaat atcaaatttg cgaacgaatc tggtatgaat  840
ctgctggatt ttgaatatgc acaagaagtc cgtgaagtgt ttcgcgataa aacggaaacc  900
atgaaagacc tgtacgaagt gctggcctca accgaatcgc agtatgatta cattaataac  960
atggtgacct catcgacaa tcacgatatg gaccgttttc aggttgcggg ctcaggtacg  1020
cgcgccaccg aacaagcgct ggcactgacg ctgacctcgc gtggcgttcc ggcgatttat  1080
tacggcaccg aacagtatat gacgggcgat ggtgacccga ataaccgcgc catgatgacg  1140
agtttcaata ccggcaccac ggcatataaa gtgattcaag cactggctcc gctgcgtaaa  1200
tccaacccgg caatcgccta cggcaccacc accgaacgtt gggtgaataa cgatgttctg  1260
attatcgaac gcaaatttgg tagttccgcg gccctggtcg ccattaatcg caactcatcg  1320
gcagcttatc cgatcagtgg tctgctgagc agcctgccag cgggcaccta ctccgatgtg  1380
ctgaatggcc tgctgaatgg taacagcatt accgtgggct ctggcggtgc ggttacgaac  1440
tttaccctgg cagcgggcgg caccgcagtt tggcagtata cggctccgga aaccagcccg  1500
gcgatcggta atgtcggtcc gacgatgggc caacgggta acattgtgac gatcgatggt  1560
```

```
cgtggtttcg gcggtacggc tggcaccgtg tactttggta cgaccgcggt caccggcagt   1620
ggtattgtgt cctgggaaga tacgcagatt aaagcggtca tcccgaaagt ggcagctggc   1680
aaaaccggtg tcagcgtgaa aacgagttcc ggcaccgcca gtaatacgtt caaatccttt   1740
aacgttctga ccggtgatca ggttacggtc cgctttctgg tcaaccaagc gaataccaac   1800
tatggcacga atgtttacct ggtcggcaac gcggccgaac tgggttcctg ggacccgaat   1860
aaagccattg gtccgatgta taaccaggtt atcgcaaaat acccgagctg gtattacgat   1920
gtgagcgttc cggcgggcac caaactggac ttcaaattca ttaaaaaagg cggtggcacg   1980
gtgacctggg aaggtggcgg taaccatacc tacacgaccc cggcgagcgg cgttggcacg   2040
gtgacggtgg attggcaaaa t                                              2061
```

SEQ ID NO: 3                    moltype = AA   length = 687
FEATURE                        Location/Qualifiers
source                         1..687
                               mol_type = protein
                               organism = synthetic construct
SEQUENCE: 3
```
SPDTSVDNKV NFSTDVIYQI VTDRFADGDR TNNPAGDAFS GDRSNLKLYF GGDWQGIIDK    60
INDGYLTGMG VTALWISQPV ENITSVIKYS GVNNTSYHGY WARDFKQTND AFGDFADFQN   120
LIDTAHAHNI KVVIDFAPNH TSPADFDNPG FAENGALYDN GSLLGAYSND TAGLFHHNGG   180
TDFSTIEDGI YKNLYDLADI NHNNNAMDAY FKSAIDLWLG MGVDGIRFDA VKHMPFGWQK   240
SFVSSIYGGD HPVFTFGEWY LGADQTDGDN IKFANESGMN LLDFEYAQEV REVFRDKTET   300
MKDLYEVLAS TESQYDYINN MVTFIDNHDM DRFQVAGSGT RATEQALALT LTSRGVPAIY   360
YGTEQYMTGD GDPNNRAMMT SFNTGTTAYK VIQALAPLRK SNPAIAYGTT TERWVNNDVL   420
IIERKFGSSA ALVAINRNSS AAYPISGLLS SLPAGTYSDV LNGLLNGNSI TVGSGGAVTN   480
FTLAAGGTAV WQYTAPETSP AIGNVGPTMG QPGNIVTIDG RGFGGTAGTV YFGTTAVTGS   540
GIVSWEDTQI KAVIPKVAAG KTGVSVKTSS GTASNTFKSF NVLTGDQVTV RPLVNQANTN   600
YGTNVYLVGN AAELGSWDPN KAIGPMYNQV IAKYPSWYYD VSVPAGTKLD FKFIKKGGGT   660
VTWEGGGNHT YTTPASGVGT VTVDWQN                                       687
```

SEQ ID NO: 4                    moltype = DNA   length = 2061
FEATURE                        Location/Qualifiers
source                         1..2061
                               mol_type = other DNA
                               organism = synthetic construct
SEQUENCE: 4
```
tcaccggaca cctcagtgga caataaagtt aacttcagca ccgatgttat ctaccagatc    60
gtcacggacc gttttgcgga tggtgaccgc accaacaatc cggcaggcga tgctttcagc   120
ggtgaccgtt ctaatctgaa actgtatttt ggcggtgatt ggcagggcat tatcgataaa   180
attaacgacg gttacctgac cggcatgggt gtgacggcgc tgtggatcag ccaaccggtg   240
gaaaacatca cctcagttat caaatactcg ggcgtcaaca atacgtctta tcatggttac   300
tgggcccgtg attttaaaca gaccaacgac gcgtttggcg atttcgccga ctttcaaaat   360
ctgattgata ccgcacatgc tcacaacatt aaagtggtta tcgatttcgc cccgaaccac   420
acctctccgg cagattttga caatccgggc tttgcagaaa atggtgctct gtatgataac   480
ggctcactgc tgggtgcata tcgaatgac accgctggcc tgttccatca caacggcggt   540
acggatttta gtaccattga agacggtatc tataaaaatc tgtacgatct ggctgacatc   600
aaccataaca ataacgcgat ggatgcctat ttcaaatcag caattgacct gtggctgggc   660
atgggtgttg atggcatccg ctttgacgcg gtcaaacaca tgccgttcgg ttggcagaaa   720
tcgtttgtga gcagcattta tggcggtgat caccgtggttt ttaccttcgg cgaatggtat   780
ctgggtgctg atcagacgga tggcgacaat atcaaatttg cgaacgaatc tggtatgaat   840
ctgctggatt ttgaatatgc acaagaagtc cgtgaagtgt ttcgcgataa aacgggaaacc   900
atgaaagacc tgtacgaagt gctggcctca accgaatcgc agtatgatta cattaataac   960
atggtgacct tcatcgacaa tcacgatatg gaccgttttc aggttgcggg ctcaggtacg   1020
cgcgccaccg aacaagcgct ggcactgacg ctgacctcgc gtggcgttcc ggcgatttat   1080
tacggcaccg aacagtatat gacgggcgat ggtgacccga ataaccgcgc catgatgacg   1140
agtttcaata ccggcaccac ggcatataaa gtgattcaag cactggctcc gctgcgtaaa   1200
tccaacccgg caatcgccta cggcaccacc accgaacgtt gggtgaataa cgatgttctg   1260
attatcgaac gcaaatttgg tagttccgcg gccctggtcg ccattaatcg caactcatcg   1320
gcagcttatc cgatcagtgg tctgctgagc agcctgccag cgggcaccta ctccgatgtg   1380
ctgaatggcc tgctgaatgg taacagcatt accgtgggct ctggcggtgc ggttacgaac   1440
tttaccctgg cagcgggcgg caccggcagtt tggcagtata cggctccgga aaccagcccg   1500
gcgatcggta tgtcggtcc gacgatgggc caaccgggta cattgtgac gatcgatggt   1560
cgtggtttcg gcggtacggc tggcaccgtg tactttggta cgaccgcggt caccggcagt   1620
ggtattgtgt cctgggaaga tacgcagatt aaagcggtca tcccgaaagt ggcagctggc   1680
aaaaccggtg tcagcgtgaa aacgagttcc ggcaccgcca gtaatacgtt caaatccttt   1740
aacgttctga ccggtgatca ggttacggtc cgctttctgg tcaaccaagc gaataccaac   1800
tatggcacga atgtttacct ggtcggcaac gcggccgaac tgggttcctg ggacccgaat   1860
aaagccattg gtccgatgta taaccaggtt atcgcaaaat acccgagctg gtattacgat   1920
gtgagcgttc cggcgggcac caaactggac ttcaaattca ttaaaaaagg cggtggcacg   1980
gtgacctggg aaggtggcgg taaccatacc tacacgaccc cggcgagcgg cgttggcacg   2040
gtgacggtgg attggcaaaa t                                              2061
```

SEQ ID NO: 5                    moltype = AA   length = 687
FEATURE                        Location/Qualifiers
source                         1..687
                               mol_type = protein
                               organism = synthetic construct
SEQUENCE: 5
```
SPDTSVDNKV NFSTDVIYQI VTDRFADGDR TNNPAGDAFS GDRSNLKLYF GGDWQGIIDK    60
INDGYLTGMG VTALWISQPV ENITSVIKYS GVNNTSYHGY WARDFKQTND AFGDFADFQN   120
```

```
LIDTAHAHNI KVVIDFAPNH TSPADRDNPG FAENGALYDN GSLLGAYSND TAGLFHHNGG   180
TDFSTIEDGI YKNLYDLADI NHNNNAMDAY FKSAIDLWLG MGVDGIRFDA VKHMPFGWQK   240
SFVSSIYGGD HPVFTFGEWY LGADQTDGDN IKFANESGMN LLDFEYAQEV REVFRDKTET   300
MKDLYEVLAS TESQYDYINN MVTFIDNHDM DRFQVAGSGT RATEQALALT LTSRGVPAIY   360
YGTEQYMTGD GDPNNRAMMT SFNTGTTAYK VIQALAPLRK SNPAIAYGTT TERWVNNDVL   420
IIERKFGSSA ALVAINRNSS AAYPISGLLS SLPAGTYSDV LNGLLNGNSI TVGSGGAVTN   480
FTLAAGGTAV WQYTAPETSP AIGNVGPTMG QPGNIVTIDG RGFGGTAGTV YFGTTAVTIS   540
GIVSWEDTQI KAVIPKVAAG KTGVSVKTSS GTASNTFKSF NVLTGDQVTV RFLVNQANTN   600
YGTNVYLVGN AAELGSWDPN KAIGPMYNQV IAKYPSWYYD VSVPAGTKLD FKFIKKGGGT   660
VTWEGGGNHT YTTPASGVGT VTVDWQN                                       687
```

SEQ ID NO: 6          moltype = DNA   length = 2061
FEATURE               Location/Qualifiers
source                1..2061
                      mol_type = other DNA
                      organism = synthetic construct
SEQUENCE: 6

```
tcaccggaca cctcagtgga caataaagtt aacttcagca ccgatgttat ctaccagatc   60
gtcacggacc gttttgcgga tggtgaccgc accaacaatc cggcaggcga tgctttcagc   120
ggtgaccgtt ctaatctgaa actgtatttt ggcggtgatt ggcagggcat tatcgataaa   180
attaacgacg gttacctgac cggcatgggt gtgacggcgc tgtggatcag ccaaccggtg   240
gaaaacatca cctcagttat caaatactcg ggcgtcaaca tacgtctta tcatggttac     300
tgggcccgtg attttaaaca gaccaacgac gcgtttggcg atttcgccga ctttcaaaat   360
ctgattgata ccgcacatgc tcacaacatt aaagtggtta tcgatttcgc cccgaaccac   420
acctctccgg cagatcgcga caatccgggc tttgcagaaa atggtgctct gtatgataac   480
ggctcactgc tgggtgcata ctcgaatgac accgctgacc tgttccatca caacggcggt   540
acggatttta gtaccattga agacggtatc tataaaaatc tgtacgatct ggctgacatc   600
aaccataaca ataacgcgat ggatgcctat ttcaaatcag caattgacct gtggctgggc   660
atgggtgttg atggcatccg ctttgacgcg gtcaaacaca tgccgttcgg ttggcagaaa   720
tcgtttgtga gcagcattta tggcggtgat caccgggttt ttaccttcgg cgaatggtac   780
ctgggtgctg atcagacgga tggcgacaat atcaaatttg cgaacgaatc tggtatgaat   840
ctgctggatt ttgaatatgc acaagaagtc cgtgaagtgt ttcgcgataa aacggaaacc   900
atgaaagacc tgtacgaagt gctggcctca accgaatcgc agtatgatta cattaataac   960
atggtgacct tcatcgacaa tcacgatatg gaccgttttc aggttgcggg ctcaggtacg   1020
cgcgccaccg aacaagcgct ggcactgacg ctgacctcgc gtggcgttcc ggcgatttat   1080
tacggcaccg aacagtatat gacgggcgat ggtgacccga ataaccgcgc catgatgacg   1140
agtttcaata ccggcaccac ggcatataaa gtgattcaag cactggctcc gctgcgtaaa   1200
tccaacccgg caatcgccta cggcaccacc accgaacgtt gggtgaataa cgatgttctg   1260
attatcgaac gcaaatttgg tagttccgcg gccctggtgc ccaactaatcg caactcatcg   1320
gcagcttatc cgatcagtgg tctgctgagc agcctgccag cgggcaccta ctccgatgtg   1380
ctgaatggcc tgctgaatgg taacagcatt accgtgggct ctggcggtgc ggttacgaac   1440
tttaccctgg cagcgggcgg caccgcagtt tggcagtata cggctccgga aaccagcccg   1500
gcgatcggta atgtcggtcc gacgatgggc caaccgggta acattgtgac gatcgatggt   1560
cgtggtttcg gcggtacggc tggcaccgtg tactttggta cgaccgcggt caccattagt   1620
ggtattgtgt cctgggaaga tacgcagatt aaagcggtca tcccgaaagt ggcagctggc   1680
aaaaccggtg tcagcgtgaa aacgagttcc ggcaccgcca gtaatacgtt caaatccttt   1740
aacgttctga ccggtgatca ggttacggtc cgctttctgg tcaaccaagc gaataccaac   1800
tatggcacga atgtttacct ggtcggcaac gcggccgaac tgggttcctg ggacccgaat   1860
aaagccattg gtccgatgta taaccaggtt atcgcaaaat acccgagctg gtattacgat   1920
gtgagcgttc cggcgggcac caaactggac ttcaaattca ttaaaaaagg cggtggcacg   1980
gtgacctggg aaggtggcgg taaccatacc tacacgaccc cggcgagcgg cgttggcacg   2040
gtgacggtgg attggcaaaa t                                              2061
```

SEQ ID NO: 7          moltype = AA   length = 687
FEATURE               Location/Qualifiers
source                1..687
                      mol_type = protein
                      organism = synthetic construct
SEQUENCE: 7

```
SPDTSVDNKV NFSTDVIYQI VTDRFADGDR TNNPAGDAFS GDRSNLKLYF GGDWQGIIDK   60
INDGYLTGMG VTALWISQPV ENITSVIKYS GVNNTSYHGY WARDFKQTND AFGDFADFQN   120
LIDTAHAHNI KVVIDFAPNH TSPADFDNPG FAENGALYDN GSLLGAYSND TAGLFHHNGG   180
TDFSTIEDGI YKNLYDLADI NHNNNAMDAY FKSAIDLWLG MGVDGIRFDA VKHMPFGWQK   240
SFVSSIYGGD HPVFTFGEWY LGADQTDGDN IKFANESGMN LLDFEYAQEV REVFRDKTET   300
MKDLYEVLAS TESQYDYINN MVTFIDNHDM DRFQVAGSGT RATEQALALT LTSRGVPAIY   360
YGTEQYMTGD GDPNNRAMMT SFNTGTTAYK VIQALAPLRK SNPAIAYGTT TERWVNNDVL   420
IIERKFGSSA ALVAINRNSS AAYPISGLLS SLPAGTYSDV LNGLLNGNSI TVGSGGAVTN   480
FTLAAGGTAV WQYTAPETSP AIGNVGPTMG QPGNIVTIDG RGFGGTAGTV YFGTTAVTIS   540
GIVSWEDTQI KAVIPKVAAG KTGVSVKTSS GTASNTFKSF NVLTGDQVTV RFLVNQANTN   600
YGTNVYLVGN AAELGSWDPN KAIGPMYNQV IAKYPSWYYD VSVPAGTKLD FKFIKKGGGT   660
VTWEGGGNHT YTTPASGVGT VTVDWQN                                       687
```

SEQ ID NO: 8          moltype = DNA   length = 2061
FEATURE               Location/Qualifiers
source                1..2061
                      mol_type = other DNA
                      organism = synthetic construct
SEQUENCE: 8

```
tcaccggaca cctcagtgga caataaagtt aacttcagca ccgatgttat ctaccagatc   60
```

```
gtcacggacc gttttgcgga tggtgaccgc accaacaatc cggcaggcga tgcttttcagc   120
ggtgaccgtt ctaatctgaa actgtatttt ggcggtgatt ggcagggcat tatcgataaa   180
attaacgacg gttacctgac cggcatgggt gtgacggcgc tgtggatcag ccaaccggtg   240
gaaaacatca cctcagttat caaatactcg ggcgtcaaca atacgtctta tcatggttac   300
tgggcccgtg attttaaaca gaccaacgac gcgtttaaac atttcgccga ctttcaaaat   360
ctgattgata ccgcacatgc tcacaacatt aaagtggtta tcgatttcgc cccgaaccac   420
acctctccgg cagattttga caatccgggc tttgcagaaa atggtgctct gtatgataac   480
ggctcactgc tgggtgcata ctcgaatgac accgctggcc tgttccatca caacggcggt   540
acggatttta gtaccattga agacggtatc tataaaaatc tgtacgatct ggctgacatc   600
aaccataaca ataacgcgat ggatgcctat ttcaaatcag caattgacct gtggctgggc   660
atgggtgttg atggcatccg ctttgacgcg gtcaaacaca tgccgttcgg ttggcagaaa   720
tcgtttgtga gcagcattta tggcggtgat caccCggttt ttaccttcgg cgaatggtat   780
ctgggtgctg atcagacgga tggcgacaat atcaaatttg cgaacgaatc tggtatgaat   840
ctgctggatt ttgaatatgc acaagaagtc cgtgaagtgt ttcgcgataa aacggaaacc   900
atgaaagacc tgtacgaagt gctggcctca accgaatcgc agtatgatta cattaataac   960
atggtgacct tcatcgacaa tcacgatatg gaccgttttc aggttgcggg ctcaggtacg  1020
cgcgccaccg aacaagcgct ggcactgacg ctgacctcgc gtggcgttcc ggcgatttat  1080
tacggcaccg aacagtatat gacgggcgat ggtgacccga ataaccgcgc catgatgacg  1140
agtttcaata ccggcaccac ggcatataaa gtgattcaag cactggctcc gctgcgtaaa  1200
tccaacccgg caatcgccta cggcaccacc accgaacgtt gggtgaataa cgatgttctg  1260
attatcgaac gcaaatttgg tagttccgcg gccctggtcg ccattaatcg caactcatcg  1320
gcagcttatc cgatcagtgg tctgctgagc agcctgcccg gcggcaccta ctccgatgtg  1380
ctgaatggcc tgctgaatgg taacagcatt accgtgggct ctggcggtgc ggttacgaac  1440
tttaccctgg cagcgggcgg caccgcagtt tggcagtata cggctccgga aaccagcccg  1500
gcgatcggta tgtcggtcc gacgatgggc caaccgggta acattgtgac gatcgatggt  1560
cgtggtttcg gcggtacggc tggcaccgtg tactttggtg gcacecgcgct caccattagt  1620
ggtattgtgt cctgggaaga tacgcagatt aaagcggtca tcccgaaagt ggcagctggc  1680
aaaaccggtg tcagcgtgaa aacgagttcc ggcaccgcca gtaatacgtt caaatccttt  1740
aacgttctga ccggtgatca ggttacggtc cgctttctgg tcaaccaagc gaataccaac  1800
tatggcacga atgtttacct ggtcggcaac gcggccgaac tgggttcctg ggacccgaat  1860
aaagccattg gtccgatgta taaccaggtt atcgcaaaat acccgagctg gtattacgat  1920
gtgagcgttc cggcgggcac caaactggac ttcaaaattca ttaaaaaagg cggtggcacg  1980
gtgacctggg aaggtggcgg taaccatacc tacacgaccc cggcgagcgg cgttggcacg  2040
gtgacggtgg attggcaaaa t                                            2061
```

```
SEQ ID NO: 9              moltype = AA   length = 687
FEATURE                  Location/Qualifiers
source                   1..687
                         mol_type = protein
                         organism = synthetic construct
SEQUENCE: 9
SPDTSVDNKV NFSTDVIYQI VTDRFADGDR TNNPAGDAFS GDRSNLKLYF GGDWQGIIDK   60
INDGYLTGMG VTALWISQPV ENITSVIKYS GVNNTSYHGY WARDFKQTND AFGDFADFQN  120
LIDTAHAHNI KVVIDFAPNH TSPADFNNPG FAENGALYDN GSLLGAYSND TAGLFHHNGG  180
TDFSTIEDGI YKNLYDLADI NHNNNAMDAY FKSAIDLWLG MGVDGIRFDA VKHMPFGWQK  240
SFVSSIYGGD HPVFTFGEWY LGADQTDGDN IKFANESGMN LLDFEYAQEV REVFRDKTET  300
MKDLYEVLAS TESQYDYINN MVTFIDNHDM DRFQVAGSGT RATEQALALT LTSRGVPAIY  360
YGTEQYMTGD GDPNNRAMMT SFNTGTTAYK VIQALAPLRK SNPAIAYGTT TERWVNNDVL  420
IIERKFGSSA ALVAINRNSS AAYPISGLLS SLPAGTYSDV LNGLLNGNSI TVGSGGAVTN  480
FTLAAGGTAV WQYTAPETSP AIGNVGPTMG QPGNIVTIDG RGFGGTAGTV YFGTTAVTIS  540
GIVSWEDTQI KAVIPKVAAG KTGVSVKTSS GTASNTFKSF NVLTGDQVTV RFLVNQANTN  600
YGTNVYLVGN AAELGSWDPN KAIGPMYNQV IAKYPSWYYD VSVPAGTKLD FKFIKKGGGT  660
VTWEGGGNHT YTTPASGVGT VTVDWQN                                      687
```

```
SEQ ID NO: 10            moltype = DNA   length = 2061
FEATURE                  Location/Qualifiers
source                   1..2061
                         mol_type = other DNA
                         organism = synthetic construct
SEQUENCE: 10
tcaccggaca cctcagtgga caataaagtt aacttcagca ccgatgttat ctaccagatc   60
gtcacggacc gttttgcgga tggtgaccgc accaacaatc cggcaggcga tgctttcagc  120
ggtgaccgtt ctaatctgaa actgtatttt ggcggtgatt ggcagggcat tatcgataaa  180
attaacgacg gttacctgac cggcatgggt gtgacggcgc tgtggatcag ccaaccggtg  240
gaaaacatca cctcagttat caaatactcg ggcgtcaaca atacgtctta tcatggttac  300
tgggcccgtg attttaaaca gaccaacgac gcgtttggcg atttcgccga ctttcaaaat  360
ctgattgata ccgcacatgc tcacaacatt aaagtggtta tcgatttcgc cccgaaccac  420
acctctccgg cagattttaa taatccgggc tttgcagaaa atggtgctct gtatgataac  480
ggctcactgc tgggtgcata ctcgaatgac accgctggcc tgttccatca caacggcggt  540
acggatttta gtaccattga agacggtatc tataaaaatc tgtacgatct ggctgacatc  600
aaccataaca ataacgcgat ggatgcctat ttcaaatcag caattgacct gtggctgggc  660
atgggtgttg atggcatccg ctttgacgcg gtcaaacaca tgccgttcgg ttggcagaaa  720
tcgtttgtga gcagcattta tggcggtgat caccCggttt ttaccttcgg cgaatggtat  780
ctgggtgctg atcagacgga tggcgacaat atcaaatttg cgaacgaatc tggtatgaat  840
ctgctggatt ttgaatatgc acaagaagtc cgtgaagtgt ttcgcgataa aacggaaacc  900
atgaaagacc tgtacgaagt gctggcctca accgaatcgc agtatgatta cattaataac  960
atggtgacct tcatcgacaa tcacgatatg gaccgttttc aggttgcggg ctcaggtacg 1020
cgcgccaccg aacaagcgct ggcactgacg ctgacctcgc gtggcgttcc ggcgatttat 1080
tacggcaccg aacagtatat gacgggcgat ggtgacccga ataaccgcgc catgatgacg 1140
```

```
agtttcaata ccggcaccac ggcatataaa gtgattcaag cactggctcc gctgcgtaaa     1200
tccaacccgg caatcgccta cggcaccacc accgaacgtt gggtgaataa cgatgttctg     1260
attatcgaac gcaaatttgg tagttccgcg gccctggtcg ccattaatcg caactcatcg     1320
gcagcttatc cgatcagtgg tctgctgagc agcctgccag cgggcaccta ctccgatgtg     1380
ctgaatggcc tgctgaatgg taacagcatt accgtggcct ctggcggtgc ggttacgaac     1440
tttaccctgg cagcgggcgg caccgcagtt tggcagtata cggctccgga aaccagcccg     1500
gcgatcggta atgtcggtcc gacgatgggc caaccgggta acattgtgac gatcgatggt     1560
cgtggtttcg gcggtacggc tggcaccgtg tactttggta cgaccgcggt caccattagt     1620
ggtattgtgt cctgggaaga tacgcagatt aaagcggtca tcccgaaagt ggcagctggc     1680
aaaaccggtg tcagcgtgaa aacgagttcc ggcaccgcca gtaatacgtt caaatccttt     1740
aacgttctga ccggtgatca ggttacggtc cgctttctgg tcaaccaagc gaataccaac     1800
tatggcacga atgtttacct ggtcggcaac gcggccgaac tgggttcctg ggacccgaat     1860
aaagccattg gtccgatgta taaccaggtt atcgcaaaat acccgagctg gtattacgat     1920
gtgagcgttc cggcgggcac caaactggac ttcaaattca ttaaaaaagg cggtggcacg     1980
gtgacctggg aaggtggcgg taaccatacc tacacgaccc cggcgagcgg cgttggcacg     2040
gtgacggtgg attggcaaaa t                                               2061

SEQ ID NO: 11                  moltype = DNA  length = 24
FEATURE                        Location/Qualifiers
source                         1..24
                               mol_type = other DNA
                               organism = synthetic construct
SEQUENCE: 11
tctccggcag attttgacaa tccg                                            24

SEQ ID NO: 12                  moltype = DNA  length = 24
FEATURE                        Location/Qualifiers
source                         1..24
                               mol_type = other DNA
                               organism = synthetic construct
SEQUENCE: 12
cggattgtca aaatctgccg gaga                                            24

SEQ ID NO: 13                  moltype = DNA  length = 24
FEATURE                        Location/Qualifiers
source                         1..24
                               mol_type = other DNA
                               organism = synthetic construct
SEQUENCE: 13
accgcggtca ccattagtgg tatt                                            24

SEQ ID NO: 14                  moltype = DNA  length = 24
FEATURE                        Location/Qualifiers
source                         1..24
                               mol_type = other DNA
                               organism = synthetic construct
SEQUENCE: 14
aataccacta atggtgaccg cggt                                            24

SEQ ID NO: 15                  moltype = DNA  length = 24
FEATURE                        Location/Qualifiers
source                         1..24
                               mol_type = other DNA
                               organism = synthetic construct
SEQUENCE: 15
tctccggcag attttgacaa tccg                                            24

SEQ ID NO: 16                  moltype = DNA  length = 24
FEATURE                        Location/Qualifiers
source                         1..24
                               mol_type = other DNA
                               organism = synthetic construct
SEQUENCE: 16
cggattgtca aaatctgccg gaga                                            24

SEQ ID NO: 17                  moltype = DNA  length = 24
FEATURE                        Location/Qualifiers
source                         1..24
                               mol_type = other DNA
                               organism = synthetic construct
SEQUENCE: 17
accgcggtca ccattagtgg tatt                                            24

SEQ ID NO: 18                  moltype = DNA  length = 24
FEATURE                        Location/Qualifiers
source                         1..24
                               mol_type = other DNA
                               organism = synthetic construct
SEQUENCE: 18
```

-continued

```
aataccacta atggtgaccg cggt                                         24

SEQ ID NO: 19              moltype = DNA  length = 24
FEATURE                    Location/Qualifiers
source                     1..24
                           mol_type = other DNA
                           organism = synthetic construct
SEQUENCE: 19
tctccggcag attttaataa tccg                                         24

SEQ ID NO: 20              moltype = DNA  length = 24
FEATURE                    Location/Qualifiers
source                     1..24
                           mol_type = other DNA
                           organism = synthetic construct
SEQUENCE: 20
cggattatta aaatctgccg gaga                                         24

SEQ ID NO: 21              moltype = DNA  length = 24
FEATURE                    Location/Qualifiers
source                     1..24
                           mol_type = other DNA
                           organism = synthetic construct
SEQUENCE: 21
accgcggtca ccattagtgg tatt                                         24

SEQ ID NO: 22              moltype = DNA  length = 24
FEATURE                    Location/Qualifiers
source                     1..24
                           mol_type = other DNA
                           organism = synthetic construct
SEQUENCE: 22
aataccacta atggtgaccg cggt                                         24

SEQ ID NO: 23              moltype = DNA  length = 41
FEATURE                    Location/Qualifiers
source                     1..41
                           mol_type = other DNA
                           organism = synthetic construct
SEQUENCE: 23
cagcaaatgg gtcgcggatc ctcaccggac acctcagtgg a                      41

SEQ ID NO: 24              moltype = DNA  length = 41
FEATURE                    Location/Qualifiers
source                     1..41
                           mol_type = other DNA
                           organism = synthetic construct
SEQUENCE: 24
gtggtggtgg tggtgctcga gattttgcca atccaccgtc a                      41
```